United States Patent [19]

Suga

[11] Patent Number: 4,627,287

[45] Date of Patent: Dec. 9, 1986

[54] LIGHT-RESISTANCE TESTER FOR MAINTAINING UNIFORM TEMPERATURE AT SURFACE OF SAMPLE

[76] Inventor: Shigeru Suga, 20-2, Yoyogi 5-chome, Shibuya-ku, Tokyo, Japan

[21] Appl. No.: 746,845

[22] Filed: Jun. 20, 1985

[30] Foreign Application Priority Data

Oct. 20, 1984 [JP] Japan ................................ 59-226766

[51] Int. Cl.⁴ ............................................ G01N 17/00
[52] U.S. Cl. .................................... 73/865.6; 73/159
[58] Field of Search .............. 73/432 SD, 159, 432 R; 374/57, 45

[56] References Cited

U.S. PATENT DOCUMENTS

| 2,810,836 | 10/1957 | Hutgens | 73/159 |
| 3,488,681 | 1/1970 | Mita et al. | 73/159 |
| 3,983,742 | 10/1976 | Suga | 73/432 SD |
| 4,544,995 | 10/1985 | Suga | 73/432 SD |

Primary Examiner—Stewart J. Levy
Assistant Examiner—Robert R. Raevis
Attorney, Agent, or Firm—Wenderoth, Lind & Ponack

[57] ABSTRACT

A light resistance tester for maintaining a uniform temperature of the surface of a sample being tested has a testing chamber, a light source mounted in the center of the testing chamber, an annular sample mounting frame positioned around the light source and rotatable around the light source as the center of rotation, and an air circulation blower mounted in the lower portion of the testing chamber below the sample mounting frame and circulating air upwardly in the testing chamber toward the sample mounting frame. An air flow divider is positioned between the sample mounting frame and the light source for dividing the upward flow of air from the air circulation blower into a portion flowing in an upward path within the sample mounting frame and spaced inwardly from samples mounted on the frame and around the light source, and a portion flowing along an upward path along the outside of the sample mounting frame.

5 Claims, 11 Drawing Figures

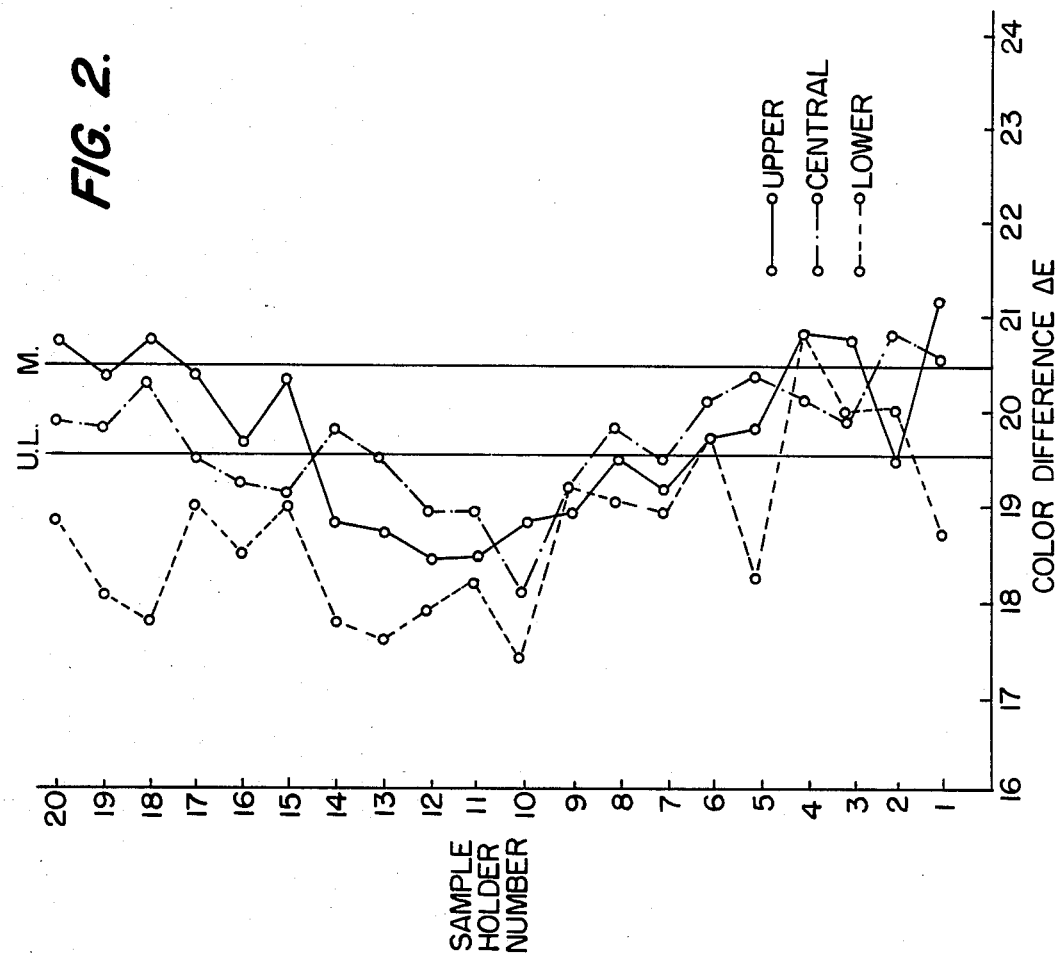
FIG. 2.
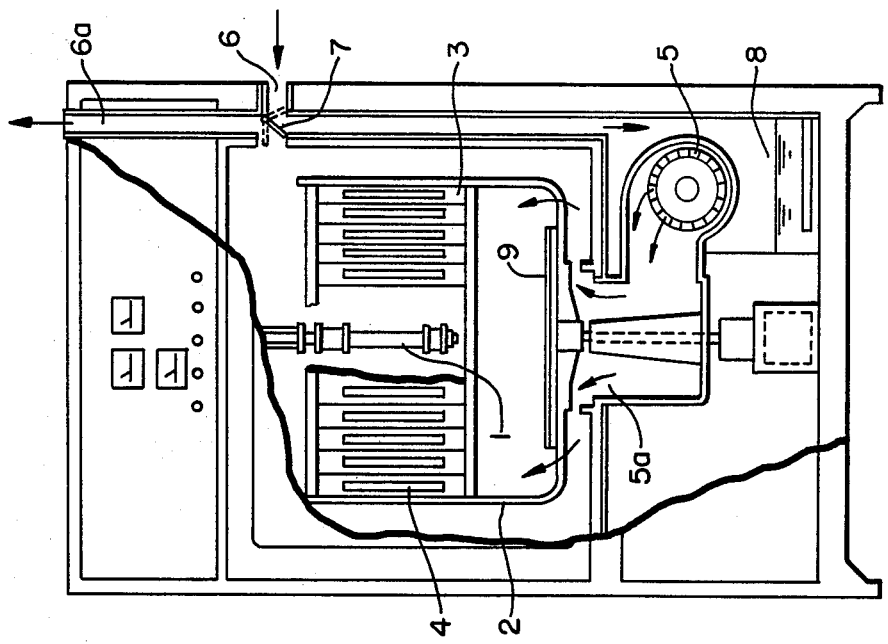
FIG. I.
(PRIOR ART)

LIGHT-RESISTANCE TESTER FOR MAINTAINING UNIFORM TEMPERATURE AT SURFACE OF SAMPLE

BACKGROUND OF THE INVENTION

1. Field of the Invention

The present invention relates to an improvement in a tester which is employed for testing the resistance of fibers, dyed goods and paints, etc., to the effects of light and it includes means to make the surface temperature of the exposed surface of each sample uniform by providing a flow divider in the lower region of a sample-setting frame and thereby directing an air-flow for regulating the temperature and humidity toward the back sides of samples and the circumference of a radiation (or light) source (typical lamp is a xenon lamp) rather than toward the exposed surfaces of the samples, so that the light-resistance test is performed under the condition of uniform temperature of the samples themselves which is most important for obtaining valid results.

2. Prior Art

In a conventional light-resistance tester, as shown in FIG. 1, a light source such as a xenon lamp 1 is provided in a testing chamber, sample holders 3 are mounted on a sample-rotating frame 2 which rotates around the lamp 1, and light from lamp 1 is applied to samples 4 mounted in the sample holders. The light resistance of the samples is determined by observing the degree of fading. Since the air in the testing chamber rises due to heat from the light source during the test, outside air is introduced by a blower 5 into the testing chamber through an air inlet 6 at the upper part of the chamber and downwardly and through a constant humidity tank 8 so as to lower the temperature in the testing chamber. An air-baffle plate 9 is provided below the sample holders to divert the air laterally from inlet opening 5a to just beneath the inside surface of the sample holders 4 so that the air rises past the ends of the baffle plate 9 along the surfaces of the sample holders, i.e. the surfaces of the samples, from the circumference of the plate 9, and flows out through vent 6a.

When the temperature inside the testing chamber reaches a prescribed level, an air regulator 7 in the air inlet 6 moves to a position indicated by the dotted lines to close inlet 6 and stop the introduction of outside air, and consequently the air coming out of the testing chamber flows from the constant humidity tank 8 along the surfaces of the samples and back down through the blower in a continuous circulation. The air regulator 7 works also as a temperature regulator, and it is opened and closed to carry out the controlling operation.

Since the air from the blower flows along the surfaces of samples, the surface temperature of the samples is affected by the temperature of this air. When the air regulator 7 is set to introduce outside air, the temperature in the constant humidity tank falls, though only for a very short time. Consequently, the temperature of the air flowing along the surfaces of the samples falls temporarily and fluctuates. If the temperature of the outside air is 20° C. when it is desired that the temperature in the testing chamber be adjusted to 40° C., for instance, the surface temperature of the samples varies from 57° to 59° C., i.e. by 2° C., due to the opening and closing of the air regulator, though only for a very short time. This is a first fault of the conventional light-resistance tester.

The air flowing over the surfaces of samples rises while being heated by a light energy from the xenon lamp 1. Hence, the temperature of the air is higher along the upper region of the samples and lower along the lower region thereof, and thus the temperature is not uniform in the upper and lower regions of the samples. Actual measurement has showed that there is a temperature difference of 5° to 6° C. between the upper and lower regions of the samples. This is a second fault of this tester.

A temperature difference also occurs between samples, and thus the temperature of all of them is not uniform. Studies by the present inventor disclosed that this non-uniformity was caused by the gaps formed between adjacent sample holders. When the sample holders are nearest to the air regulator 7, for instance, the circulating air flows through said gaps, and thus the air flowing over the surface of the sample, and hence the surface temperature, is not uniform. The temperature difference between samples is further increased by the presence or absence of said gaps and the difference in the dimensions thereof. This is a third fault of the conventional tester.

When there is a temperature difference between the surfaces of the samples, the color difference value representing the degree of fading due to the test varies, even if the light energy of the source (the xenon lamp) is applied at a prescribed strength and for the same time duration. Therefore, the step of changing the position of the sample holder or turning it over during the course of the test has been taken heretofore so as to reduce the effect of the non-uniformity of the temperature. Whether or not a light-resistance tester gives normal fading color difference values is examined by using xenon blue standard cloth which is issued by AATCC (American Association for Textile Chemists and Colorists). FIG. 2 shows the results of a test conducted for 20 sheets of this cloth. The U.L line indicates the standard value for the upper and lower portions of the sample, which value is 19.5, and M the standard value for the intermediate portion thereof, which value is 20.5. It is seen from this figure that measured values deviate considerably from the straight U.L line of standard fading color difference values and the straight M line thereof, and intersect these lines depending on the position of the same around the periphery of the sample rotating frame. The measured values are clearly not at all uniform.

As described above, the nonuniformity of the fading color difference is related to the nonuniformity of the temperature values. Thus, uniform temperature is a requisite for obtaining accurate results from the test.

SUMMARY OF THE INVENTION

After analyzing the prior art apparatus and the problems thereof as described above and finding the cause of nonuniformity of the temperature, the present inventor has managed to eliminate said nonuniformity of the temperature by providing a flow divider in the lower region of a sample-holder setting frame so that the circulating air can flow through the central part of the tester around the xenon lamp without contacting the surfaces of samples, thereby substantially eliminating the nonuniformity of temperature due to such circulating air.

BRIEF DESCRIPTION OF THE DRAWINGS

FIG. 1 is an elevation view partly broken away of a prior art light resistance tester;

FIG. 2 is a graph showing the results of tests conducted with the apparatus of FIG. 1;

DETAILED DESCRIPTION OF THE PREFERRED EMBODIMENT

Figure 3:
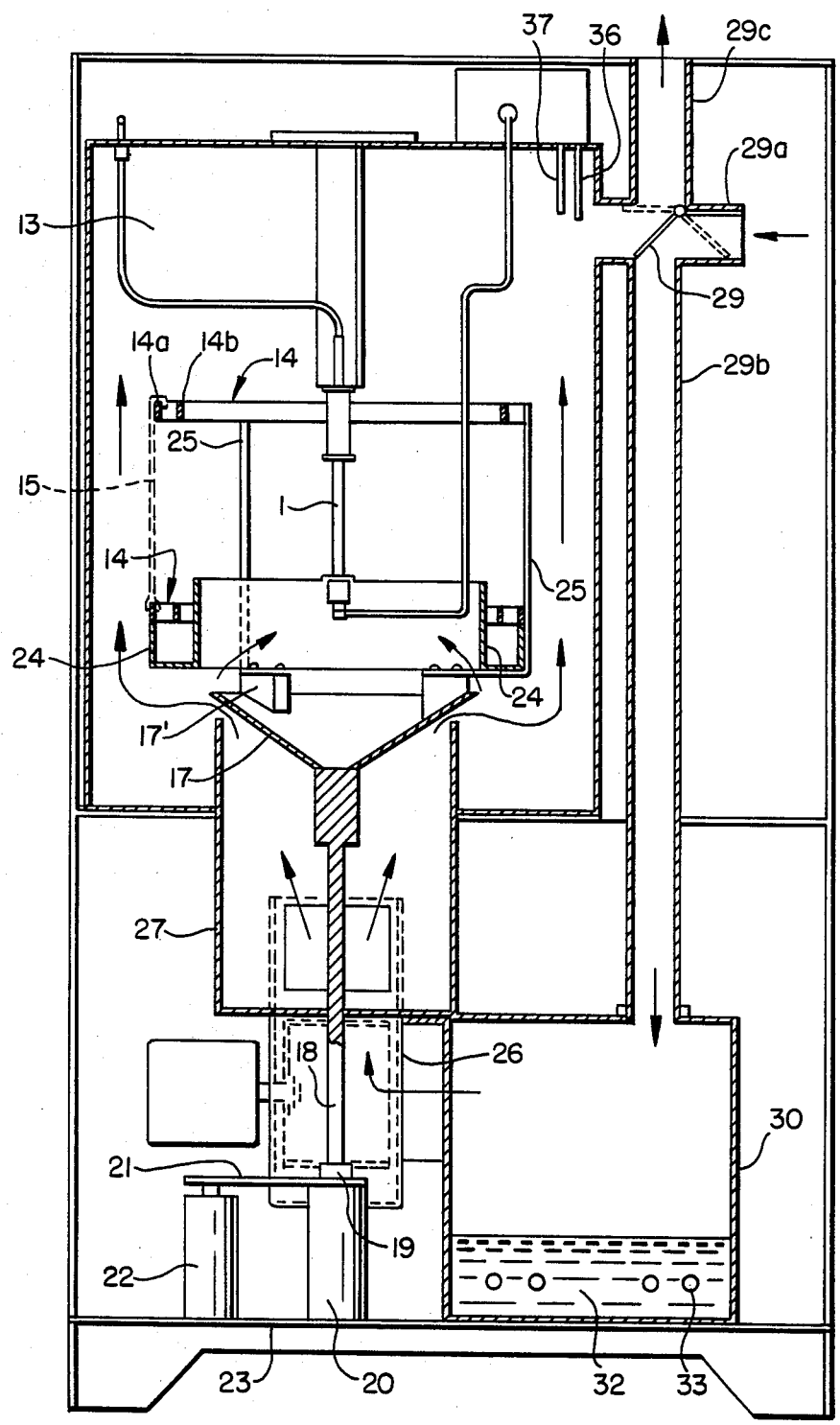
FIG. 3 is a sectional elevational view of the light-resistance tester of the present invention.
Figure 4:
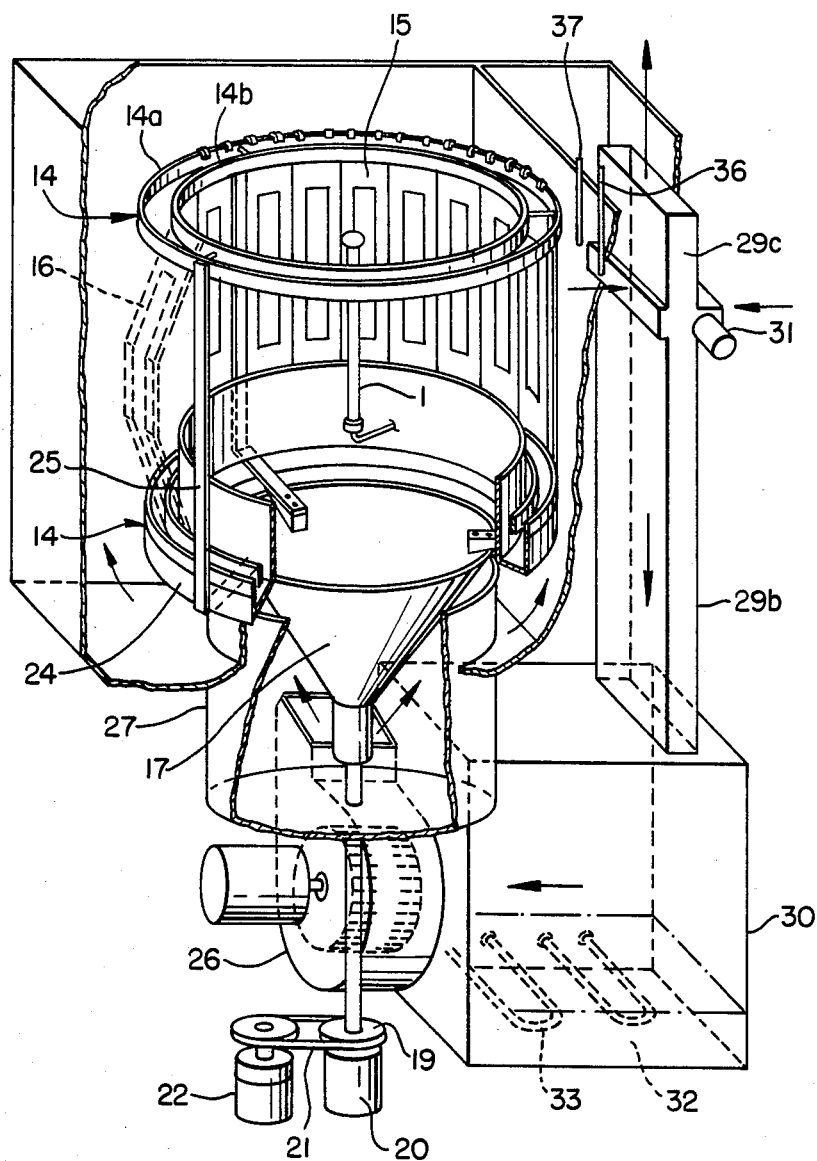
FIG. 4 is a schematic perspective view, partly broken away, of the tester of the present invention.
Figure 6:
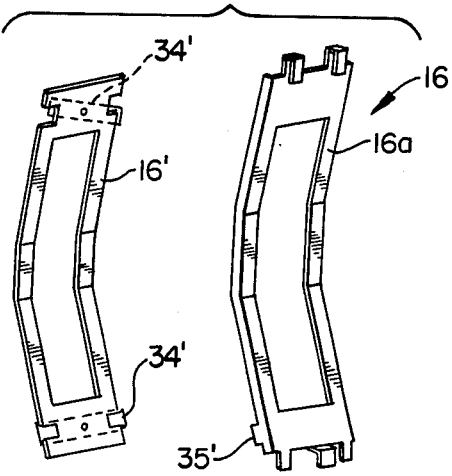
FIG. 6 is an exploded perspective view of an outwardly bowed sample holder.
Figure 7:
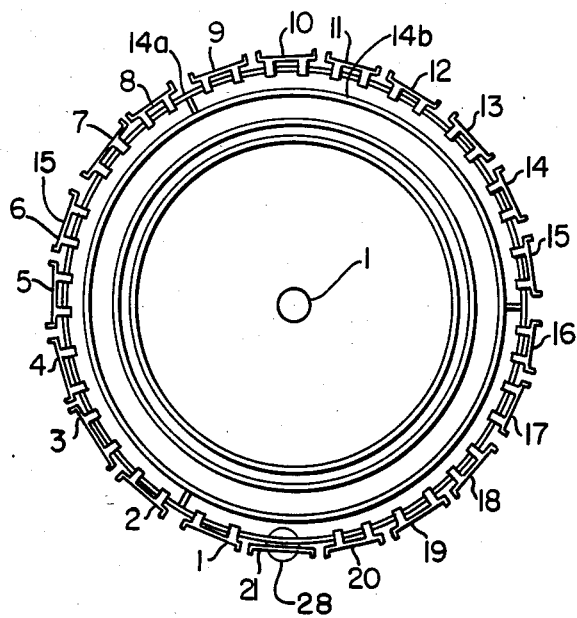
FIG. 7 is a plan view of the sample rotating frame with the flat sample holders mounted thereon.
Figure 8:
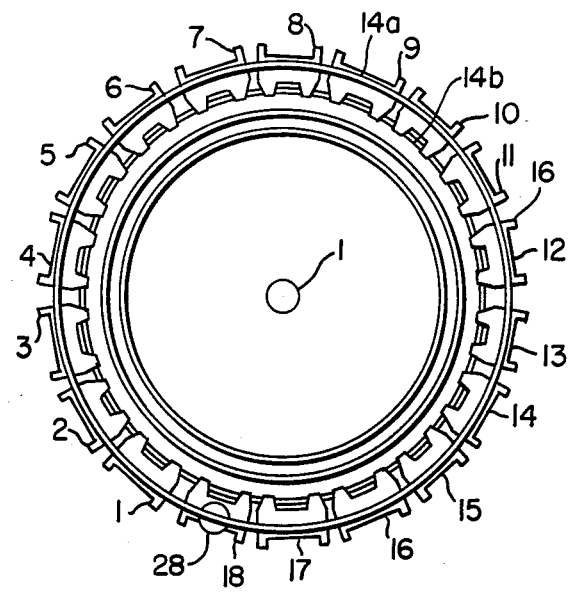
FIG. 8 is a plan view of the sample rotating frame with the lowered sample holders mounted thereon.

As seen in FIGS. 3 and 4, a xenon lamp 1 is suspended in the central part of a testing chamber 13, and a frame 14 on which sample holders are mounted is provided around the lamp. The frame 14 comprises two sets of inner and outer concentric rings 14a and 14b positioned, an upper set and a lower set, and vertical supporting rods 25 connecting these sets of rings to each other. When flat sample holders 15 (shown by dotted lines in FIG. 3 and by solid lines in FIG. 4) are used, they are mounted on the outer rings, and in the case of the bowed sample holders 16 (shown by the lines in FIG. 6 and by phantom lines in FIG. 4), they are mounted on the inner rings. FIG. 7 is a plan view showing the flat sample holders 15 mounted on the outer rings 14a. Twenty-one holders are used in this case. FIG. 8 is a plan view showing the bowed sample holders 16 mounted on the inner rings 14b. Eighteen holders are used in this case. Numeral 28 denotes a black panel thermometer mounted on outer rings 14a, while the encircled numerals denote the positions of the holders in the peripheral direction around the frame. The frame 14 is held on projections 17' which are provided on the upper portion of a rotary body 17. The rotary body 17 has a funnel-shape and serves to introduce air flowing from a blower 26 and air duct 27 around the shaft 18 and having the upper end of the air duct spaced from rotary body 17 to form an air discharge opening toward a flow divider 24 and to rotate the frame 14. The rotating shaft 18 is supported by a bearing 20 through a sprocket 19 and is connected to a motor 22 by a chain 21. The bearing and the motor are mounted on a base 23.

The flow divider 24, which is an essential component of the present invention, comprises a double cylinder, the inner cylinder of which is higher than the outer cylinder thereof, and a ring-shaped base plate connecting the lower ends of the cylinders, and the cross-section thereof is shaped in the form of a U with unequal legs. The outer cylinder is positioned in the lower portion of the frame 14 and the supporting rods 25. The inner cylinder is positioned inside the surfaces of samples and spaced therefrom so that the air flowing and rising from below will not contact said surfaces. The diameter of the inner cylinder is slightly larger than the outside diameter of the rotary body 17, and the height thereof is limited to a height such that the light of the xenon lamp 1 can reach the samples without a shadow being cast on the lower portions thereof. The air from the blower 26 passes through the air duct box 27, flows out of discharge opening formed between the rotary body 17 and the upper end of the air duct box, and flows further toward the flow divider 24. Most of this air flows along the outer cylinder and over the back side of the samples, maintaining the temperature of the samples. A relatively small amount of the air flows along the inner cylinder and around the circumference of the lamp while cooling the lamp, but not contacting the surfaces of the samples. The air divided by the flow divider joins in the upper portion of the testing chamber. In the normal position of an air regulator 29 in air inlet 29a in the upper portion of testing chamber 13, shown in dotted lines, the air flows back down through duct 29b through constant humidity tank 30 to the blower 26 and to the flow divider. The temperature inside the testing chamber is detected by a detecting element 36, e.g. a thermometer, controlling the regulator 29. When the temperature rises, the air regulator 29 is moved to the position shown in the solid lines by motor 31 to let the outside air in, and the air from the upper part of chamber 13 is exhausted through vent 29c, and when the temperature reaches the prescribed level, the air regulator 29 is moved back to the position indicated by the dotted lines for recirculating the air. The humidity is detected by a detecting unit 37, e.g. a wet-bulb thermometer, and the water 32 in the constant humidity tank 30 is heated by a heater 33.

Figure 5:
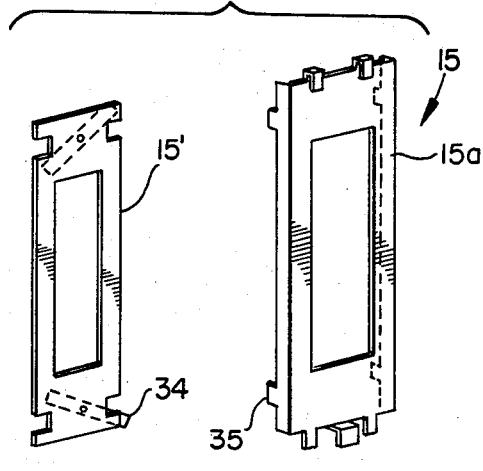
FIG. 5 is an exploded perspective view of a flat sample holder.
Figure 11:
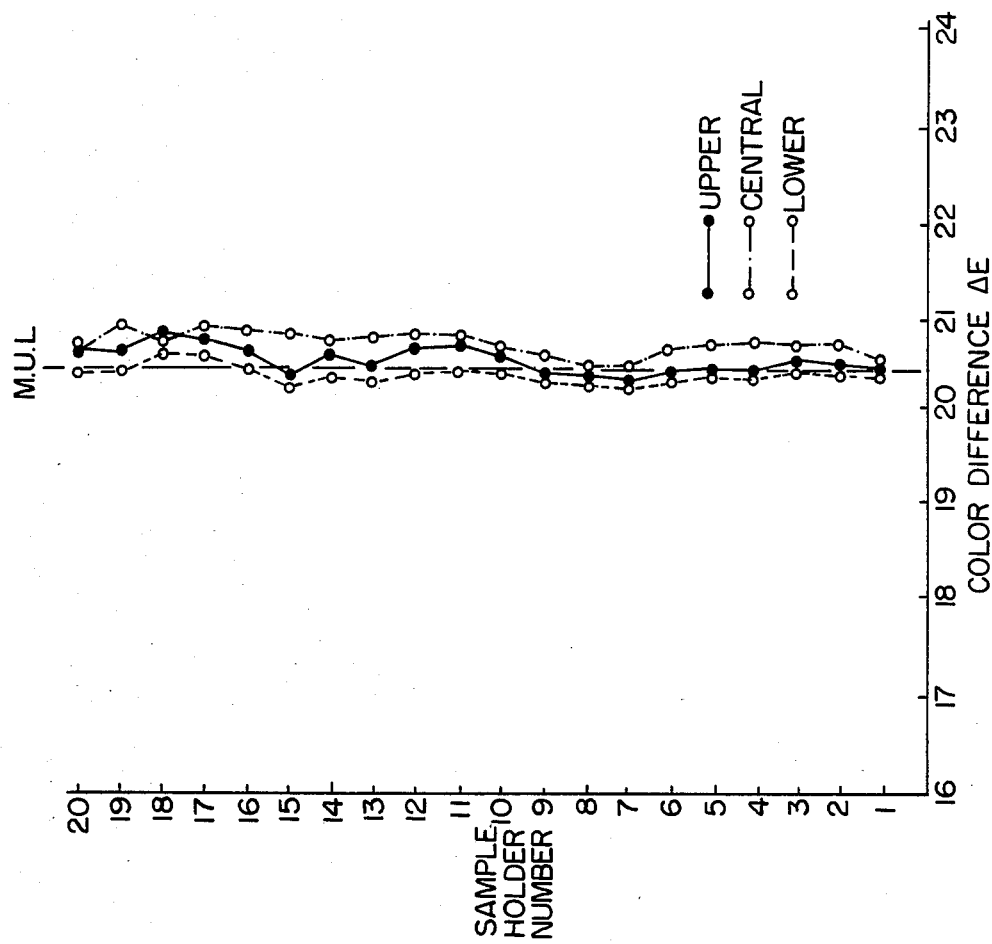
FIG. 11 is a graph showing the results of a test operation of the apparatus according to the present invention using the bowed sample holders.

The apparatus is constructed so that either flat sample holders 15 such as are usually employed, or bowed sample holders 16 can be employed. When the flat sample holders 25 are employed, each sample is put between the main body 15a of the holder and a presser plate 15' and held by a spring plate 34 and a spring seat 35, as shown in FIG. 5. The flat holder 15, when mounted on the frame 14, receives different amounts of light from the light source 1 according to the positions thereon. The light is directed as indicated by the arrows in the figure, and the central region of the sample, nearest to the light source, receives the light perpendicularly to the surface thereof, while the energy of the light received by the upper and lower regions of the sample is at an angle to the surface, and therefore somewhat less intense. Hence, if blue standard cloth is tested by using this holder under conditions such that the surface temperature of the sample is uniform, color difference values thus obtained will be found on the two straight lines UL and M in FIGS. 2 and 10. The bowed holder 16 has the upper and lower portions inclined outwardly as shown in FIG. 6 so that the light will be received substantially perpendicularly to the sample therein at the upper, central and lower portions. In this holder, the sample is held between the main body 16a of the holder and a presser plate 16'. When said blue standard cloth is tested by using this inclined holder under conditions such that the surface temperature of the sample is uniform, the values for the results of the test will fall on one straight line M.U.L. as shown in FIG. 11.

Figure 9:
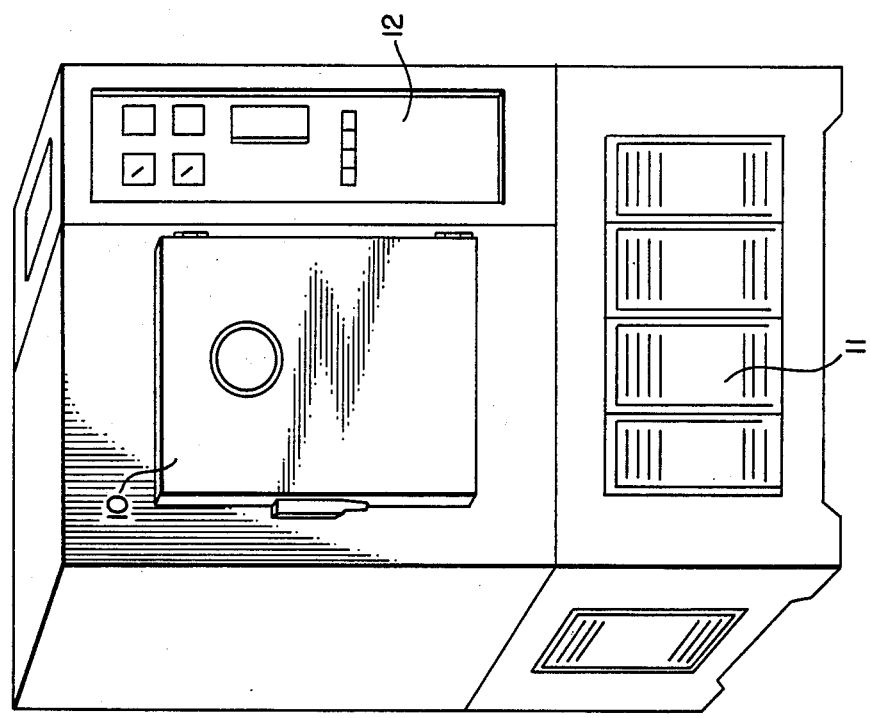
FIG. 9 is a front perspective view of the light-resistance tester of the present invention.

FIG. 9 is a perspective view of the tester shown in FIG. 3, showing a door 10 provided on the front of the main body, with the testing chamber is inside of it. The blower, a rotating mechanism and the constant humidity tank are installed behind a cover 11 in the lower portion of the main body. An operation panel 12 is equipped with instruments to sense conditions and control the operation of the tester.

As described previously, the flow divider 24 which is the essential component of the present invention operates so as not to let air flow along the exposed surface of the sample. Therefore, the temperature difference among the upper, central and lower regions of the surface of the sample is very small, and a change in the temperature of the air caused by opening and closing the air regulator 29 has no effect since the air does not directly contact the exposed surface of the sample.

The ratio of the quantities of air allowed to flow along the back side of the sample and around the circumference of the lamp 1 is another essential point of the construction of the present invention for maintaining uniformity of temperature of the samples, and said ratio is controlled by the following method based on a test. In the tester of the above-described embodiment, the inside diameter of the flow divider 24 is made 3 to 4 cm larger than the outside diameter of the upper end of the rotary body 17, and the height of the opening between the flow divider 24 and the rotary body 17 is made 2 to 3 cm. The ratio of the flow rate of the air flowing along the back side of samples to that flowing around the lamp 1 is about 9:1 to 7:3. The test showed that this range of the ratios of the flow was best.

Next, an example of measurement of the surface temperature of a sample will be described, with measured values obtained by a conventional tester for reference. The example shows that the difference in the surface temperature is 1 C.° or less according to the present invention, while it is 6 C.° at the maximum according to the conventional tester.

|  |  | Surface temperature (°C.) according to the present invention |  | Surface temperature (°C.) according to conventional tester |
|---|---|---|---|---|
| Flat sample holder | upper portion | 57 | upper portion | 59 |
|  | central | 58 | central | 58 |
|  | lower | 57 | lower | 53 |
| Inclined sample holder | upper portion | 58 | upper portion | 59 |
|  | central | 58 | central | 58 |
|  | lower | 57.5 | lower | 55 |

No temperature difference is caused on the surface of the sample by the opening and closing of the air regulator 29. Also, even when the sample holder comes near the air regulator, since most of the air flows along the back side of samples, no air flows through the gaps between adjacent holders and the temperature does not change.

Figure 10:
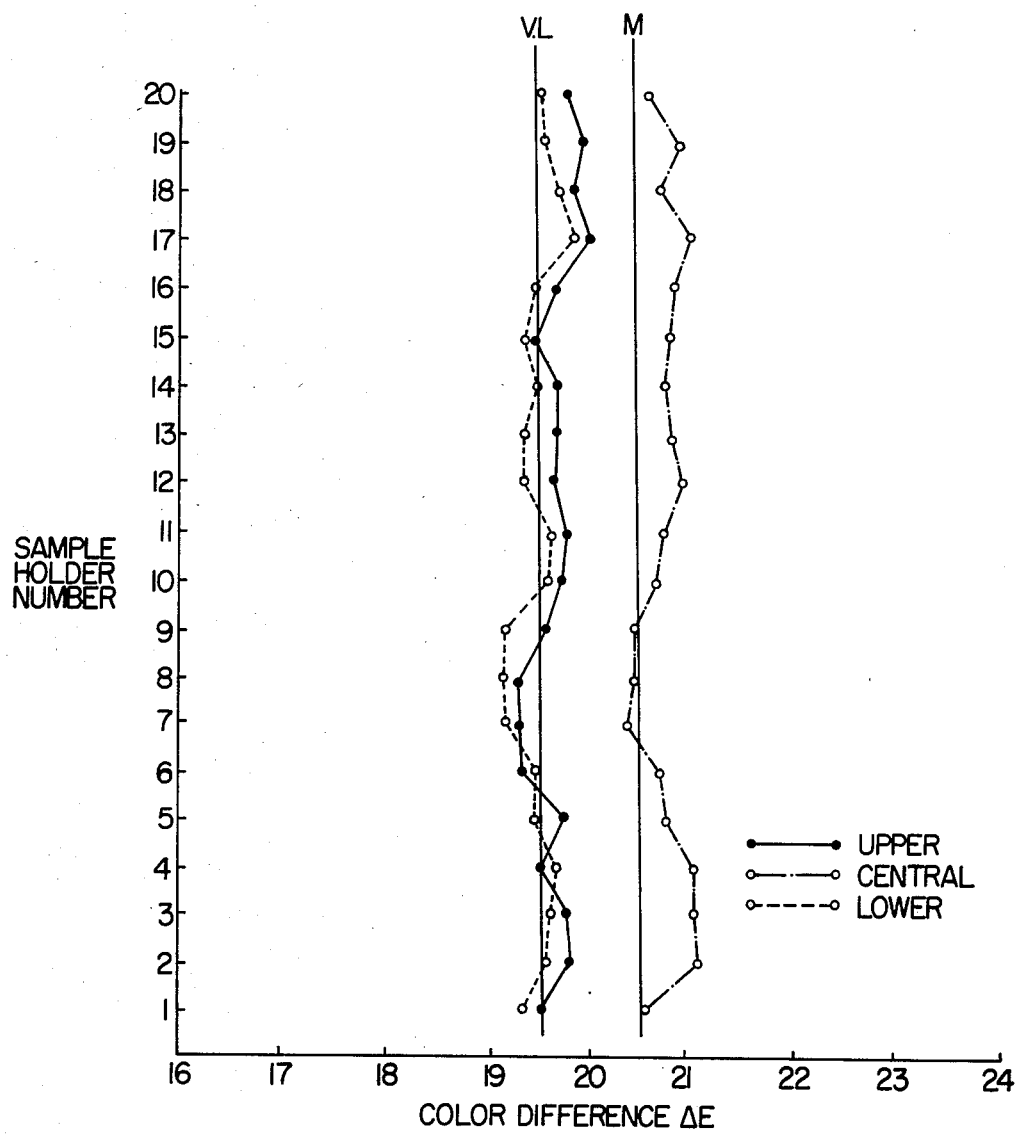
FIG. 10 is a graph showing the results of a test operation of the apparatus according to the present invention using the flat sample holders.

A fading test was conducted by using the xenon blue standard cloth, which has been described, as a reference, and the results shown in FIGS. 10 and 11 were obtained. FIG. 10 shows the results of a test in which the flat holders 15 were used. The deviation from standard fading color difference values was 0.6 or less, and the nonuniformity among twenty samples was 1 at the maximum, and thus very excellent results were obtained in comparison with the usual results shown in FIG. 2. In the case where the bowed sample holders 16 were used, as shown in FIG. 11 the deviation was 0.5 or less, which is also excellent uniformity.

What is claimed is:

1. A light resistance tester for maintaining a uniform temperature of the surface of a sample being tested, comprising:
   a testing chamber;
   a light source mounted in the center of said testing chamber;
   an annular sample mounting frame positioned around said light source and rotatable around said light source as the center of rotation;
   air circulation means mounted in the lower portion of said testing chamber below said sample mounting frame and circulating air upwardly in said testing chamber toward said sample mounting frame; and
   an air flow divider between said sample mounting frame and said light source for dividing the upward flow of air from said air circulation means into a portion flowing in an upward path within said sample mounting frame and spaced inwardly from samples mounted on said frame and around said light source, and a portion flowing along an upward path along the outside of said sample mounting frame.

2. A light resistance tester as claimed in claim 1 in which said sample mounting frame has upper and lower annular ring means, and sample holders mounted between said ring means, and said air flow divider comprises an annular divider immediately below said lower ring means and having an inner cylinder spaced inwardly from the inner periphery of said lower ring means and extending upwardly past said lower ring means.

3. A light resistance tester as claimed in claim 2 in which said air circulation means comprises a blower in the lower part of said testing chamber and a rotary body between said blower and said divider having a funnel-shaped member at the upper end with an outer diameter slightly less than the inner diameter of said annular divider.

4. A light resistance tester as claimed in claim 3 in which said sample holders are flat.

5. A light resistance tester as claimed in claim 3 in which said sample holders are bowed outwardly of said sample mounting frame.

* * * * *